United States Patent [19]

Fiege et al.

[11] 4,245,126

[45] Jan. 13, 1981

[54] PROCESS FOR THE PREPARATION OF A MIXTURE OF 2- AND 4-HYDROXYBENZYL ALCOHOL

[75] Inventors: Helmut Fiege, Leverkusen; Karlfried Wedemeyer, Cologne; Kurt Bauer; Reiner Mölleken, both of Holzminden, all of Fed. Rep. of Germany

[73] Assignee: Bayer Aktiengesellschaft, Leverkusen, Fed. Rep. of Germany

[21] Appl. No.: 71,427

[22] Filed: Aug. 30, 1979

[30] Foreign Application Priority Data

Jul. 14, 1979 [DE] Fed. Rep. of Germany ....... 2928554

[51] Int. Cl.³ .............................................. C07C 39/11
[52] U.S. Cl. ..................................................... 568/764
[58] Field of Search ......................................... 568/764

[56] References Cited

U.S. PATENT DOCUMENTS

| 2,802,882 | 8/1957 | Bader et al. | 568/764 |
| 2,839,587 | 6/1958 | Raum | 568/764 |

FOREIGN PATENT DOCUMENTS 558987  1/1944  United Kingdom ..................... 568/764

OTHER PUBLICATIONS

The Merck Index, 9th Ed., 1976, pp. 778 and 779.
U.S.S.R. Journal Plast. Massy, 1971, (6), pp. 11–13.

*Primary Examiner*—Joseph E. Evans
*Attorney, Agent, or Firm*—Sprung, Felfe, Horn, Lynch & Kramer

[57] ABSTRACT

Mixtures of 2- and 4-hydroxybenzyl alcohol with high contents of 4-hydroxybenzyl alcohol are obtained by a process comprising reacting phenol with paraformaldehyde in the presence of a compound which exhibits two or more tertiary nitrogen atoms per molecule and a $pK_a$ value of $\geq 6.5$ (measured at 20° C. in water).

7 Claims, No Drawings

PROCESS FOR THE PREPARATION OF A MIXTURE OF 2- AND 4-HYDROXYBENZYL ALCOHOL

The invention relates to a process for the preparation of a mixture of 2- and 4-hydroxybenzyl alcohol.

The reaction of phenol with formaldehyde in the presence of strongly basic catalysts is known. Thus for example in the U.S.S.R. Journal Plast. Massy 1971 (6), pp. 11-13 (see Chem. Abstr. Vol 75, 77564 t) a process is described for the preparation of phenol formaldehyde resins by the reaction of phenol and formaldehyde in which ammonia or hexamethylene tetramine are used as strongly basic catalysts. As is clear from the examination of the reaction products the use of ammonia or hexamethylene tetramine leads to the formation of amine compounds.

A process for the preparation of mixtures of 2- and 4-hydroxybenzyl alcohol is described in DE-OS (German Published Specification) 2,729,075. In this process, the mixtures are obtained in high space/time yields by reaction of phenol and paraformaldehyde in the presence of strongly basic catalysts. However, the proportion of 4-hydroxybenzyl alcohol in these mixtures is only about 30% by weight, relative to the hydroxybenzyl alcohols present in the reaction mixture.

Since 4-hydroxybenzyl alcohol is an important starting material for the preparation of 4-hydroxybenzaldehyde, there was a need to prepare mixtures of 2- and 4-hydroxybenzyl alcohol containing a higher proportion of 4-hydroxybenzyl alcohol.

It has been found, surprisingly, that the proportion of 4-hydroxybenzyl alcohol in the said hydroxybenzyl alcohol mixtures can be increased considerably if the reaction of phenol with paraformaldehyde is conducted in the presence of basic compounds which exhibit two or more tertiary nitrogen atoms per molecule and a $pK_a$ value of $\geq 6.5$ (measured at 20° C. in water).

The invention thus relates to a process for the production of mixtures of 2- and 4-hydroxybenzyl alcohol by the reaction of phenol with paraformaldehyde in the presence of basic catalysts, characterised in that the compounds used as basic catalysts exhibit two or more tertiary nitrogen atoms per molecule and a $pK_a$ value of $\geq 6.5$ (measured at 20° C. in water).

The $pK_a$ value, which is used in the process according to the invention to describe the basic strength of the basic nitrogen compounds to be employed is the negative logarithm of the acidic dissociation constant $K_a$ of the corresponding nitrogen atom ($pK_a = \log K_a$; for the definition of the $pK_a$ and the acidic dissociation constants $K_a$ see D. D. Perrin "Dissociation Constants of Organic Bases in Aqueous Solution", Butterworths London 1965, pp. 1-4). In this as well as in other tabular compilations numerous compounds suitable for the process according to the invention, together with their $pK_a$ values, are mentioned. Compounds with several nitrogen atoms possess, as is known, several $pK_a$ values. The appropriate value as far as the invention is concerned is always the highest $pK_a$ value.

The following may be mentioned as examples of those compounds with several tertiary nitrogen atoms and a $pK_a$ value of $\geq$ (i.e. equal to or higher than) 6.5 which are to be used according to the invention:

(A) peralkylated open-chained, monocyclic or bicyclic di- or polyamines and (B) N,N'-substituted mono- and bicyclic amidines.

Of the compounds of type A those peralkylated open-chained, monocyclic or bicyclic di- or polyamines of the formulae:

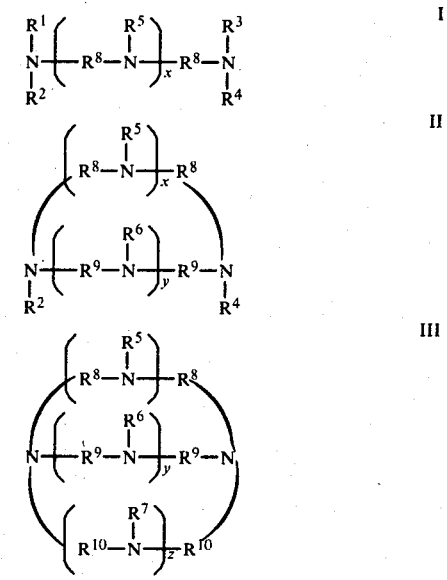

have proven to be particularly suitable.

In the formulae I, II and III:

$R^1$, $R^2$, $R^3$, $R^4$, $R^5$, $R^6$ and $R^7$ represent, independently of each other, $C_1$-$C_{12}$-alkyl, or cycloalkyl groups optionally substituted by $C_1$-$C_4$-alkyl groups, $R^8$, $R^9$ and $R^{10}$ represent, independently of each other, $C_2$-$C_6$-alkylene or cycloalkylene groups, x, y and z represent, independently of each other, an integer of 0 to 10.

Of the compounds of type B, N,N-substituted mono- or bicyclic amidines of the formulae:

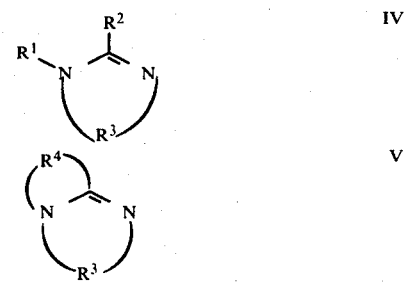

have proven to be particularly suitable.

In the formulae IV and V:

$R^1$ represents a $C_1$-$C_{12}$-alkyl group or a cycloalkyl group optionally substituted by $C_1$-$C_4$-alkyl groups, $R^2$ represents hydrogen, a $C_1$-$C_{12}$-alkyl group or a cycloalkyl group optionally substituted by $C_1$-$C_4$-alkyl groups, $R^3$ represents a $C_xH_{2x}$- or $C_xH_{2x-2}$-group, in which x represents an integer from 2 to 4, and $R^4$ represents a $C_yH_{2y}$-group, in which y represents an integer from 3 to 7.

Of the compounds of the formulae I, II and III those compounds are preferred in which $R^1$ to $R^7$ are identical and denote, for example, a methyl, ethyl, propyl, isopropyl, n-butyl, isobutyl, sec.-butyl, tert.-butyl, pentyl, hexyl or cyclohexyl group and in which $R^8$ to $R^{10}$ are identical and denote, for example, an ethylene, 1,2-propylene, 1,3-proylene, 1,2-butylene, 1,3-butylene, 1,4-butylene, 2,3-butylene, 1,4-pentylene or 2,3-pentyl group.

Particularly preferred, in the case of formula I, are compounds with x=0 to 5, in the case of formula II compounds with x=0 to 5 and y=0 and in the case of formula III compounds in which x, y and z denote an integer from 0 to 5.

As far as compounds of the formula I are concerned, those are particularly preferred which are easily accessible from alkylene di- and polyamines able to be produced on an industrial scale [see Ullmann's "Encyclopädie der technischen Chemie" (Encyclopaedia of industrial chemistry), 4th edition 1974, vol. 7, pp. 382-383] by peralkylation of the hydrogen atoms of the nitrogen (see Houben-Weyl, 3rd edition 1957, vol. 11/1, pp. 641-645). Examples which may be mentioned in particular are: tetramethyl ethylene diamine, pentamethyl diethylene triamine, hexamethyl triethylene tetramine, heptamethyl tetraethylene pentamine, tetramethyl propylene 1,2-diamine, tetramethyl propylene 1,3-diamine, pentamethyl dipropylene diamine, hexamethyl tripropylene triamine.

Of the compounds of formula II those particularly preferred are: 1,4-dialkylpiperazines, such as 1,4-dimethylpiperazine or 1,4-diethylpiperazine and peralkylated aza crown ethers such as tetramethyl-1,5,9,13-tetraazacyclohexadecane or hexamethyl-1,4,7,10,13,16-hexaazacyclo-octadecane.

Of the peralkylated, bicyclic di- or polyamines of formula III triethylene triamine (1,4-diazabicyclo[2,2,2]-octane) is particularly suitable because of the ease of its industrial accessibility.

Of the compounds of formula IV those are preferred in which $R^1$ denotes a methyl, ethyl, propyl, isopropyl, n-butyl, isobutyl, sec.-butyl, tert.-butyl, pentyl, hexyl or cyclohexyl group, $R^2$ denotes hydrogen or a methyl, ethyl, propyl, isopropyl, n-butyl, sec.-butyl, tert.-butyl, pentyl, hexyl or cyclohexyl group (and which can be identical to or different from $R^1$) and $R^3$ represents a vinylene group or a 1,3-propylene group.

The following may be particularly emphasised as examples of compounds of the formula IV because of the ease of their industrial accessibility: 1-methyl-1H-imidazole, 1,2-dimethyl-1H-imidazole and 1,4,5,6-tetrahydro-1,2-dimethyl-pyrimidine.

Of the compounds of formula V those bicyclic amidines are preferred, because of their ease of accessibility, in the formula of which $R^3$ denotes an ethylene or 1,3-propylene group and $R^4$ denotes a 1,3-propylene, 1,4-butylene, 1,5-amylene or 1,7-heptylene group. The following may be mentioned as examples: 2,3,5,6-tetrahydro-7H-pyrrolo-[1,2-a]imidazole, (x=2; y=3); 2,3,4,6,7,8-hexahydro-pyrrolo-[1,2-a]pyrimidine, (x=3; y=3); 2,3,4,5,7,8-hexahydro-9H-pyrrolo-[1,2-a]-[1,3]-diazepine (x=4 y=3); 3,4,6,7,8,9-hexahydro-2H-pyrido-[1,2-a]-pyrimidine (x=3; y=4); 2,3,4,6,7,8,9,10-octahydro-pyrimido-[1,2-a]-azepine (x=3; y=5); 2,3,4,6,7,8,9,10,11,12-decahydropyrimido-[1,2-a]-azonine (x=3; y=7).

The following are particularly preferred: 2,3,4,6,7,8-hexahydropyrrolo-[1,2-a]-pyrimidine (x=3; y=3) and 2,3,4,6,7,8,9,10-octahydro-pyrimido-[1,2-a]-azepine (x=3; y=5).

The catalysts to be used according to the invention are used in an amount of from 0.0001 to 0.05 mols, preferably 0.0005 to 0.02 mols per mol of phenol.

In the process according to the invention phenol and paraformaldehyde are used in a molar ratio of 5:1 to 15:1, preferably in the molar ratio 8:1 to 12:1.

The catalysts to be used according to the invention may be added all at the same time to the reaction components at the beginning of the reaction. It is also possible to first add one portion of the catalyst at the beginning of the reaction and subsequently to add the remainder continuously or intermittently during the course of the reaction.

The process according to the invention is advantageously conducted at temperatures of 25° to 125° C., preferably from 40° to approximately 100° C. The reaction time is generally between 0.5 and 10 hours.

The reaction mixture can be worked up, as described in DE-OS (German Published Specification) No. 2,729,075, by distilling off some of the excess phenol and isolating the 2- and 4-hydroxybenzyl alcohols by counter-current extraction.

EXAMPLES 1 to 10

In order to conduct the experiments in each case 10 mols of phenol and 1 mol of paraformaldahyde are heated, whilst stirring and adding the quantity stated in the table of the catalyst stated in the table, to the reaction temperature stated in the table. The reaction mixture was kept at the reaction temperature for the reaction time stated in the table.

The reaction was terminated when the polarographically determined conversion of formaldehyde was 85% to 98%. The composition of the reaction mixture obtained in this way was determined by high pressure liquid chromatography or, after conversion of the components of the reaction mixture into their trimethylsilyl derivatives via N-methyl-N-trimethylsilyl-acetamide, by gas chromatography.

The analysis of the hydroxybenzyl alcohol mixtures produced during the reactions showed the proportions mentioned in the table of 2- and 4-hydroxybenzyl alcohol.

TABLE

| Example no. | Catalyst [pK$_a$ value at 20° C. in H$_2$O] (mol/mol of pheonol) | Reaction temp. (°C.) | Reaction time [h] for (%) conversion of CH$_2$O | Yield (% of th.) rel. to CH$_2$O used | 2-hydroxybenzyl alcohol | 4-hydroxybenzyl alcohol |
|---|---|---|---|---|---|---|
| 1 | tetramethyl ethylene diamine [9.2] (0.002) | 70 | 8 (98) | 82 | 59 | 41 |
| 2 | pentamethyl diethylene triamine [9.4] | 70 | 3 (98) | 85 | 54 | 46 |

TABLE-continued

| Example no. | Catalyst [pK$_a$ value at 20° C. in H$_2$O] (mol/mol of pheonol) | Reaction temp. (°C.) | Reaction time [h] for (%) conversion of CH$_2$O | Yield (% of th.) rel. to CH$_2$O used | 2-hydroxybenzyl alcohol | 4-hydroxybenzyl alcohol |
|---|---|---|---|---|---|---|
| 3 | 1,4-dimethyl piperazine [7,8] (0,002) | 70 | 8 (85) | 67 | 64 | 36 |
| 4 | triethylene diamine [8,2] (0,002) | 70 | 9 (98) | 85 | 60 | 40 |
| 5 | 1-methyl-1H-imidazole [6,8] (0,002) | 70 | 8 (89) | 73 | 56 | 44 |
| 6 | 1,2-dimethyl-1H-imidazole [7,9] (0,002) | 70 | 7 (97) | 85 | 57 | 43 |
| 7 | 1,4,5,6-tetrahydro-1,2-dimethyl pyrimidine [10,2] (0,002) | 70 | 3 (98) | 85 | 54 | 46 |
| 8 | 2,3,4,6,7,8-hexahydro-pyrolo[1,2-a]-pyrimidine [9,6] (0,02) | 70 | 4 (98) | 84 | 53 | 47 |
| 9 | 2,3,4,6,7,8-hexahydro-pyrolo[1,2-a]-pyrimidine [9,6] (0,0008) | 80 | 3,5 (98) | 83 | 53 | 47 |
| 10 | 2,3,4,6,7,8,9,10-octahydro-pyrimido[1,2-a]-azepine [9,8] (0,00066) | 90 | 1,3 (98) | 85 | 52 | 48 |
| 11* | hexamethylene tetramine [6,3] (0,002) | 70 | 2 (98) | 70 | 70 | 30 |
| 12* | potassium hydroxide (0,002) | 60 | 5 (98) | 85 | 70 | 30 |

*comparison examples

What is claimed is:

1. In the known process for the preparation of a mixture of 2- and 4-hydroxybenzyl alcohol by reacting phenol with paraformaldehyde in the presence of a basic catalyst, the improvement comprising using as basic catalyst a compound which exhibits two or more tertiary nitrogen atoms per molecule and a pK$_a$ value of $\geq 6.5$ (measured at 20° C. in water).

2. The process according to claim 1, wherein a peralkylated open-chained monocyclic or bicyclic di- or polyamine is used as catalyst.

3. The process according to claim 1, wherein tetramethyl ethylene diamine, pentamethyl diethylene triamine, hexamethyl triethylene tetramine, 1,3-dimethylpiperazine or triethylene triamine is used as catalyst.

4. The process according to claim 1, wherein a N,N'-substituted mono- or bicyclic amidine is used as catalyst.

5. The process according to claim 1, wherein 1-methyl-1H-imidazole, 1,2-dimethyl-1H-imidazole, 1,4,5,6-tetrahydro-1,2-dimethyl-pyrimidine, 2,3,4,6,7,8-hexahydro-pyrrolo-[1,2-a]-pyrimidine or 2,3,4,6,7,8,9,10-octahydro-pyrimido-[1,2-a]-azepine is used as catalyst.

6. The process according to claim 1, wherein the catalyst is used in an amount of 0.0001 to 0.05 mol per mol of phenol.

7. The process according to claim 1, wherein the catalyst is used in an amount of 0.0005 to 0.02 mol per mol of phenol.

* * * * *